United States Patent
Dzneladze et al.

(10) Patent No.: US 6,350,474 B1
(45) Date of Patent: Feb. 26, 2002

(54) PHOSPHATE COMPOSITION AND ITS UTILIZATION

(76) Inventors: David Dzneladze; Andro Dzneladze; Nargisa Jabishvili, all of Building 4, Apt. #112, Block 5, Vazha Pshavela Avenue, Tbilisi 380086 (GE)

(*) Notice: Subject to any disclaimer, the term of this patent is extended or adjusted under 35 U.S.C. 154(b) by 0 days.

(21) Appl. No.: 09/202,340
(22) PCT Filed: Jun. 14, 1996
(86) PCT No.: PCT/GE96/00001
§ 371 Date: Jun. 7, 1999
§ 102(e) Date: Jun. 7, 1999
(87) PCT Pub. No.: WO97/47201
PCT Pub. Date: Dec. 18, 1997

(51) Int. Cl.[7] .................. A01N 59/00; A01N 59/26; A01N 59/16; A01N 59/06; C09D 5/10
(52) U.S. Cl. .................. 424/605; 424/600; 424/601; 424/602; 424/603; 424/604; 424/617; 424/639; 424/641; 424/646; 424/647; 424/648; 424/682; 424/684; 424/685; 424/690; 424/691; 424/698; 422/28; 106/14.12; 106/14.21; 252/387
(58) Field of Search .................. 424/601, 604, 424/605, 639, 641, 647, 648, 600, 602, 603, 617, 646, 682, 684, 685, 690, 691, 698; 422/28; 106/14.12, 14.21; 252/387

(56) References Cited

U.S. PATENT DOCUMENTS

| | | | |
|---|---|---|---|
| 4,817,333 A | 4/1989 | Szepessy et al. | 47/58.1 |
| 5,242,488 A * | 9/1993 | Stetson et al. | 106/14.12 |
| 5,279,650 A * | 1/1994 | Stetson et al. | 106/14.12 |

FOREIGN PATENT DOCUMENTS

| | | |
|---|---|---|
| DE | 2302216 | 8/1974 |
| DE | 3039437 | 5/1982 |
| GB | 1250341 | 10/1971 |
| WO | 94/04167 | 3/1984 |

OTHER PUBLICATIONS

Soviet Patent 364575 (Abstract) Abzgil'din, et al. Dec. 28, 1972.
Soviet Patent 274696 (Abstract) Kir'yanov Jun. 24, 1970.
Soviet Patent 339,090 (Abstact) Mech. Eng. Techn. Res. Dec. 16, 1977.
Japanese 6143488 (Abstract) Nippon Steel May 24, 1994.

* cited by examiner

*Primary Examiner*—John Pak
(74) *Attorney, Agent, or Firm*—Frost Brown Todd LLC

(57) ABSTRACT

The invention deals with phosphate water solution with cold solidification capacity. Phosphate composition containing iron oxide solution in acid, water, advantages from the following properties; it contains orthophosphorus acid and in addition metal powder. Phosphate composition is ecologically pure product, non toxic, non cancerogenic, non-allergic. It has antimicrobial, antivirus and fungicidal properties. Phosphate composition can be applied within medicine: surgery, dermatology, dentistry, oncology, pharmacology and other branches. In agriculture use: as a means of curing plant diseases, within veterinary—as a means for preventive maintenance and curing of animal diseases, within construction—as an anticorrosive, fire-resistant, hydro-electric isolating covers, ceramic tiles, concretes, which protect against radiation, as well as for producing other composite materials.

5 Claims, No Drawings

PHOSPHATE COMPOSITION AND ITS UTILIZATION

This application is a 371 of PCT/GE96/00001, filed on Jun. 14, 1996.

The invention relates to fields such as medicine, agriculture, cattle-raising and construction. The invention deals with water solutions with cold solidification capacity, which are known as mineral adhesives or astringents and are synthesised oxide, phosphate or metal by means of ortho, pyro-, tri-, poly-, or any other phosphorus acid. They can be applied within medicine: surgery, dermatology, dentistry, oncology, pharmacology and other branches. In agricultural use: as a means of curing plant diseases; within veterinary—as a means for preventive maintenance and curing of animal diseases; within construction—as a anticorrosive, fire-resistant, decorative, hydro-electric isolating covers, ceramic tiles, concretes, which protect against radiation, as well as for producing other composite materials.

There are well known examples of phosphate adhesives, containing zinc and aluminium, and phosphatic adhesives containing aluminium and magnesium, which are utilised both in dentistry as a means for producing dental cements and in construction—as a means for producing fire resistant covers (1,2), through thermos treatment. The phosphate binder of calcium is used in production of toothpastes, it can be served as an ingredient of animal food, can be used for production of anticorrosive and fire resistant covers in construction, through heat processing (1,2).

There is also the example of phosphate binder, which contains iron polyphosphate, polyphosphoric acid and water (3). It is obtained through adding $Fe_2O_3$ to orthophosphoric acid and further boiling, during which the water vaporises and polycondenses and iron and tripolyphosphates emerge. Thus obtained phosphate binder is used for producing fire resistant material through heat processing.

The selected prototype for the proposed invention is the phosphate composition as a binder (4), containing iron oxide solution in polyphosphoric acid, water and in addition highmolecular polysacharide or its derivative with the following ratio of components, in massive parts: polyphosphoric acid—100, iron oxide—36–53, highmolecular polysacharide or its derivative—0.5–3.5, water—15–30. The disadvantage of the composition is the high cost of producing, resulting from: (i) the inefficient utilisation of polyphosphoric acid and electric (heat) power, (ii) the toxicity of the solution, caused by the emergence of detrimental (harmful) soluble and gaseous materials after dissolution of polysacharide in acid environment during boiling; (iii) the thermos (heat) treatment necessary for solidification are characteristic of polyphosphates.

The proposed invention envisions the reduction of the cost of producing, toxicity and the period of cold solidification through exclusion of polyphosphoric acid and polysacharide from composition contents, as well as exclusion of electric (heat) energy from the technological process.

The substitution of inefficient and expensive polyphosphoric acid with orthophosphoric acid results in a decrease of the composition cost of producing and increases the cold solidification capacity. The synthesis proceeds without supplying electric (heat) energy from outer sources, but rather by means of exothermous reaction ongoing within reaction area which causes the reduction of cost of producing. The exclusion of polysacharide from the contents of the invention results in the decrease of toxicity level.

The phosphate composition is obtained through: Adding water, while stirring continuously, iron oxide powder and any metal powder for example, aluminium to orthophosphoric acid calculated on 100% acid, for maintenance of temperature regime within the reaction area and for neutralising the extra acidity, the ratio of components in massive parts being the following:

| | |
|---|---|
| orthosphosphoric acid | 100 |
| iron oxide | 20–41 |
| metal powder | 0.5–2.5 |
| water | 30–70 |
| phosphate ion molar ratio with iron ion | 2–4 | heat liberated after the exothermal reaction (40°–50°) is enough for dissolution of iron oxide and metal powder which requires holding the mass for 2 hours. The output of the reaction represents transparent, brownish sticky liquid, compactness of which comprises 1.5 $gr/m^3$, while the ratio of phosphate ion to the iron ion equals 2.0–4.0. The solution is stable for about 2 years.

The iron oxide weight in the proposed invention above 41 will cause the dissolution and solidification of the solution, while below 41, it will result in reducing the cold solidification capacity.

Substitution of aluminium powder by any other metal powder, e.g. Fe, Ca, Mg, Zn, Co, Ni, Y, Sc etc, will alter the composition characteristics, namely, it will either increase or decrease cold solidification capacity.

The metal powder weight above 2.5 in the reaction area will heighten the temperature level to 120°–130° and will result in sticking of dissolved particles and orthophosphate anion will turn into polyphosphate. If metal powder weight is below 0.5, the temperature within the reaction area remains unaltered and the dissolution process is carried at a slow speed, over the period of several days.

The weight of water above or below the normalised level in the reaction area will violate the temperature regime.

The Table 1 and 2 below demonstrate the properties of the iron phosphate solution of a specific composition.

The phosphate composition, unlike its prototype and its analogues is characterised by bactericidal, virucidal and fungicidal properties. The recorded data show that among phosphate admixtures only copper phosphate is characterised by antimicrobial properties and its utilisation in the preparation of fungicides is recommended.

Within the proposed invention the preliminary clinical investigation of the phosphate composition is conducted at the experimental and clinical scientific research laboratory attached to the state Medical University; at the Institute of Labour Hygiene and professional diseases of the Health Ministry of Georgia; at the scientific centre dealing with particularly dangerous infections of the Institute of Sanitary and Hygiene.

The research has revealed that the phosphate composition in water solutions kill the microbes of plague, pseudotuberculosis, salmonella, colibacillus, dysentery, golden staphylococcus microbes, grippe, hepatitis, West Nile fever and oncoviruses (Table 3,4). Within 1–5 minutes after treatment the equipment, clothes, premises, laboratory vessels, patients excrements are sterilised.

As regards its toxicity, it is well known that inorganic admixtures of 5 valence phosphorus are one of the harmless admixtures for humans. Besides, the organism absorbs phosphorus in ortho-form and $PO_4^3$ anion is considered to be the one of the most significant component of a "physiologically" living organism, which regulates the buffer $HPO_4^{2-}/H_2PO_4^-$ system of blood.

The results of toxicological, pathomorphological, histological, pathophysiological, bacteriological, physiological, biochemical, neurological, immunological studies of the phosphate composition have proved that the solution does not alter cardiovascular and respiratory system parameters, neither the functions of liver and kidneys, has no impact on peripheral blood indicators and the immune status of the body, causes no change in cell. There are no indications of allergic reactions. The solution fulfils the deodorant function of dismissing unpleasant odours. Both the phosphate composition and its production processes are ecologically safe.

The abovementioned researchers have proved that the solution is neither toxic nor cancerogenic and can be used both for external use and drinking.

The Health Ministry of Georgia has authorised the application of phosphate composition in medicine. The production process is registered at Georgia Standard 13.06.95, the registration number is 15420044-001-95, it is licensed by the Municipality of Tbilisi 19.04.96.

Phosphate composition can serve as: (i) disinfecting means in medicine and in various other fields (veterinary, agriculture, etc); (ii) neutralising premises, inventory, linen, fecal masses for conducting current and final disinfections during bacterial and virus infections; (iii) a means for dealing with objects infected with bactera and viruses and those suspected of being contaminated; (iv) a means for purifying technical, drinking and fecal waters.

The Table 5 (see p. 10) indicates the amount and timing of disinfection of various objects:

The clinical research of phosphate composition is undertaken in the Republic Hospital, in the centre of sepsis and burn treatment, in the institute of urology and skin clinic. It is proved that the phosphate water solutions are characterised by strong capacity (as compared with furacycline) for preventing decomposition and inflammatory processes, of wound healing, analgesic, remedial against scratching and fungous diseases, deodorant properties. Thus it can be served as antiseptic: for treatment of wounds, various damages—burns of the skin, suppurative dermatitis, trophic ulcer, decubitus, broken skin and others. Phosphate composition is used to cure cystitis, nephritis, gastritis, colitis, cholecystitis, vaginitis, erosion, ulcer, conjuctivitis, ceratitis, gingivitis, angina, tonsilitis, pharingytis, dermatitis, eczema, psoriasis, hemorrhoids, burn, suppurative and gangrenous wounds, erysipelas, trophic ulcer, sweating, tumoral formations, oncological diseases.

The phosphate composition water solutions are used in veterinary medicine for curing animal microbial, virus, fungal diseases, such as brucellosis, anthrax, tularemia, plague.

The iron can be used in practice for curing purposes only in its organic admixtures against anaemia. Among these admixtures there are organic admixtures containing phosphorus, such as iron glycerine phosphate—insoluble in water and phytopherolactolirthic organic admixture. Both admixtures are ineffective.

With a view to effectively utilise phosphate composition for curing purposes it is possible to produce a number of preparations of various designation: pills, powders, suppositories, ointments, and ampoules.

Because of its antimicrobic and fungicidal properties, the phosphate composition can be used in agriculture and forestries as a means for fighting plant (vine, crops, fruit, citrus, vegetables) vermins and for curing microbic, virus and fungal diseases.

According to the recorded data phosphate composition materials are building materials, which are produced through warming up the composition above 300°. These materials are the following fire resistant, thermal isolating, anticorrosive and decorative covers, fire resistance concretes and ceramic materials, adhesives, etc.

The proposed invention envisions the utilisation of the phosphate composition with cold solidification capacity without thermal treatment.

1. Fire-retardant—fire resistant cover, colourless, scentless, transparent water solution, with compactness 1.15–1.10.

The principle designation of the solution is to cover the surface of building materials—wood, metal, concrete as well as textiles and papers with a view to increasing the latters' fire resistance capacity. The treatment is carried out through sprinkling, applying and dipping method. The amount of the solution for 1 $m^2$ equals to 0.2 liters (or 1 liter for 5 $m^2$). After treatment the material surface should be dried up at an indoor temperature under dry environmental conditions during 24 hours.

The solution does not damage the surface, does not alter its colour and material quality. The The solution is neither toxic nor carcinogenic. It is fire resistant and is inflammable. Apartments and mass assemblage places can be treated with the solution. Its production process is ecologically safe.

The solution is kept in a closed plastic or glass vessel. The vessels are washed with water after usage.

The expiration period of the solution is 3 years.

The fire resistance of the phosphate solution is studies by the fire hazard research department at the Ministry of Internal Affairs. The wooden, textile, paper and metal materials and the paints produced on their surface, after treatment by the solution have withstood the test designed by the state standard and thus they can be referred to as non inflammable materials.

On the basis of the above conclusions the invention related work is registered at Georgia Standard no 150044-002-96 and is licensed by the Tbilisi Municipality.

2. Anticorrosive Composition Solution

The above solution is used for removing the rust off the metal surface without preliminary mechanical treatment, and for protecting against further rusting. It is composite water solution colourless and scentless. Its compactness equals 1.4–1.5. It is applied on the rusty surface of the metal either through sprinkling or with a brush. After applying it, the rust is removed from the metal surface and protective coating is formed which can further be painted with any paint or with the same solution after adding pigment.

Anticorrosive coating, with thickness of 80–90 mkm, is characterised by high metal adhesion capacity (70–90 kg/cm$^2$), mechanical solidity (5.10$^6$M), temperature resistance (−20°–500°), independent of changes in the climate conditions. It is not inflammable.

The solution is not toxic and its production process is ecologically safe. The solution is fire resistant and is not explosive. The amount of the solution per 1 m$^2$ surface equals 0.25 liters. The solution is kept in closed plastic or glass vessel at the indoor temperature, for the period of 4–5 years.

Used instruments and vessels can be washed with water.

3. Phosphate Paint

The above paint is used for painting concrete, brick buildings, wooden articles and paper. The paint is characterised by high decorative properties, independent of changes in the climate or conditions and is a good surface adhesion. Through adding various pigments, it becomes capable of obtaining desirable colours and patterns.

The paint is applied to primed surface. The soil is prepared through diluting the same paint in water with a specific ratio. The paint amount per 1 m$^2$ is 4–5-kg.

concrete, brick etc) with brush or through sprinkling for several times. As a result of two-fold treatment the porosity is reduced by 20–30%, hardness on compression increases by 100–200%. The temperature extension index of the treated stone equals zero.

5. For producing the ceramic materials on the phosphate composition basis, the production waste and mineral raw material processing waste is added to the solution. The materials are obtained through pouring out or pressing, without warming up.

The materials are characterised by high mechanical solidity (hardness) (60), thermal stability up to 2000°, inertness towards aggressive environment and climate changes, dielectiric properties. The shape, colour and pattern could be altered according to the need.

TABLE I

| example | 100% orthophosphoric acid | iron oxide kg | metal powder kg | water kg | The ratio of phosphate to iron ion | the duration of synthesis hrs | temperature of synthesis C° |
|---|---|---|---|---|---|---|---|
| 1 | 100 | 28 | Al - 1.0 | 50 | 3.0 | 2.0 | 40–50 |
| 2 | 100 | 41 | Al - 2.5 | 70 | 2.0 | 2.5 | 50–60 |
| 3 | 100 | 20 | Al - 0.5 | 30 | 4.0 | 1.5 | 30–40 |
| 4 | 100 | 32 | Al - 1.0 | 60 | 2.5 | 2.5 | 40–50 |
| 5 | 100 | 24 | Al - 1.0 | 40 | 3.5 | 1.5 | 30–40 |
| 6 | 100 | 28 | Fe - 1.5 | 50 | 3.0 | 2.0 | 40–50 |
| 7 | 100 | 41 | Zn - 0.5 | 70 | 2.0 | 2,5 | 40–50 |
| 8 | 100 | 20 | Mg - 0.5 | 30 | 4.0 | 1.5 | 30–50 |

The paint is kept in glass or plastic vessel. The expiration period is 2–3 years. The vessels and instruments are washed with water after use.

The paint is not toxic. It is scentless. Its production is ecologically safe. The paint is fire resistant and inflammable.

4. Composite Solution for Hardening Porous Minerals

The above composite is 10–20% water solution, colourless and scentless. The compactness of it equals 1.05–1.10. It is characterised by high adhesion capacity towards a range of inorganic materials. It is solidified under any temperature and acquires water-fire resistance (up to 1000°), photochemical stability, mechanical solidity. The solution is not toxic. Its production is ecologically safe.

The protective coating is applied to the porous aluminosillicates and materials (sandstone, tufasandstone,

TABLE 2

| example | compactness gr/sm$^3$ | pH | stickiness cH$_3$ | stability in month | hardening of composition materials |
|---|---|---|---|---|---|
| known | 1.56–1.60 | 1.0–2.8 | 50–120 | 4–12 | thermos treatment |
| 1 | 1.50 | 2.70 | 60 | 24 | indoor temperature |
| 2 | 1.65 | 3.5 | 80 | 5 | indoor temperature |
| 3 | 1.45 | 2.0 | 50 | 30 | thermos treatment |
| 4 | 1.62 | 2.5 | 75 | 24 | indoor temperature |
| 5 | 1.48 | 2.50 | 50 | 20 | indoor temperature |
| 6 | 1.50 | 2.70 | 70 | 20 | indoor temperature |
| 7 | 1.65 | 3.5 | 80 | 4 | indoor temperature |
| 8 | 1.40 | 2.0 | 50 | 24 | thermos treatment |

TABLE 3

| | exposure 3 min | | | | | | exposure 5 min | | | | | | |
|---|---|---|---|---|---|---|---|---|---|---|---|---|---|
| | concentration of solution | | | | | | | | | | | | |
| microbes | 0.1 | 0.2 | 0.3 | 0.5 | 1 | 2 | 0.1 | 2.0 | 0.3 | 0.5 | 1 | 2 | control |
| plague EV | + | − | − | − | − | − | − | − | − | − | − | − | + |
| pseudotuberculosis | + | + | + | − | − | − | + | + | − | − | − | − | + |
| intestine iersiniosis | + | + | + | − | − | − | + | + | − | − | − | − | + |
| salmonella | + | + | + | − | − | − | + | + | − | − | − | − | + |
| klebsiels | + | + | + | − | − | − | + | + | − | − | − | − | + |
| vibrions (cholera) | + | − | − | − | − | − | − | − | − | − | − | − | + |
| dysentery | + | − | − | − | − | − | − | − | − | − | − | − | + |
| colibacillus | + | + | + | + | − | − | + | + | + | − | − | − | + |

TABLE 3-continued

| | exposure 3 min | | | | | | exposure 5 min | | | | | | |
|---|---|---|---|---|---|---|---|---|---|---|---|---|---|
| | concentration of solution | | | | | | | | | | | | |
| microbes | 0.1 | 0.2 | 0.3 | 0.5 | 1 | 2 | 0.1 | 2.0 | 0.3 | 0.5 | 1 | 2 | control |
| golden staphylococcus | + | + | + | + | − | − | + | + | + | + | − | − | + |
| anthrax | + | + | + | − | − | − | + | + | − | − | − | − | + |
| bruceliosis | + | + | + | − | − | − | + | + | − | − | − | − | + |

TABLE 4

| | exposure 3 min | | | | | | | exposure 5 min | | | | | |
|---|---|---|---|---|---|---|---|---|---|---|---|---|---|
| | concentration of solution | | | | | | | | | | | | |
| virus | 0.01 | 0.02 | 0.05 | 0.1 | 0.2 | 0.50 | 1 | 0.01 | 0.02 | 0.05 | 0.1 | 0.2 | 0.5 | 1 |
| West Nile Fever | + | − | − | − | − | − | − | − | − | − | − | − | − |
| grippe | + | + | + | − | − | − | − | + | + | − | − | − | − |
| coxsac B | + | + | + | + | − | − | − | + | + | + | + | − | − |
| hepatitis A | + | + | + | + | + | + | − | + | + | + | + | + | − |
| plague phage | + | − | − | − | − | − | − | − | − | − | − | − | − |
| pseudotuberculosis | − | − | − | − | − | − | − | − | − | − | − | − | − |
| oncovirus | + | + | + | − | − | − | − | − | + | − | − | − | − |

TABLE 5

| OBJECT | solution amount | timing | treatment |
|---|---|---|---|
| premises and hard inventory | 500 ml/m² | 1.0 | sprinkling, cleaning |
| lavatory pan, reservoir, bath tube, floor sweeper | 500 ml/m² | 1.0 | sprinkling, cleaning |
| fluid extracts: urine etc | twice more | 1.0 | pouring, spraying |
| window panes, tables, furniture linen, gowns, masks, gloves, rubber boots patients' vessels | 300 ml/m² | 1.0 | sprinkllng, cleaning |
| laboratory vessels: china, glass, metal hands and other exposed parts of body instruments after dissection vivarium premises | 5 lit/1 kg | 1.0 | placing in solution |
| | | 5 | cleaning |
| | 2 lit/1 set | 1.0 | placing in solution |
| | | 1.0 | placing in solution |
| | | 5 | washing |
| | | 1.0 | placing in solution |
| | 300 ml/m² | 1.0 | sprinkling |

TABLE 6

Comparison of disinfectant solution "Nargosept" to other disinfecting solutions, containing chlorine, phenolic and quat. ammonium chloride compounds

| Quality | Chlorine preparations | Phenolic | Quat. ammonium chloride | "Nargosept" |
|---|---|---|---|---|
| 1. Toxicity | yes | yes | yes | no |
| 2. Cancerogenic | yes | yes | yes | no |
| 3. Allergic | yes | yes | yes | no |
| 4. Scent | strong | specific scent | yes | scentless |
| 5. Stability | evaporative, not stable | evaporative | evaporative | stable for 5–6 years |
| 6. Influence on mucous membrane | causes strong irritation | acute inflammation | inflammation, burns | no influence |
| 7. Influence on skin | burns, causes dermatitis | acute inflammation, necrosis | redness, burns | no influence |
| 8. Influence on eyes | irritates, causes conjunctivitis | irritates, causes conjunctivitis | irritates | no influence |
| 9. Influence on respiratory ducts | irritates, causes laryngitis and pharyngitis | irritates, causes laryngitis and pharyngitis | irritates | no influence |
| 10. Influence on central nervous sys. | dizziness, vomiting and loss of orientation | paralysis of C.N.S | yes | no influence |
| 11. Poisoning | causes acute poisoning | causes acute poisoning | yes | no influence |
| 12. Bactericidal and virucidal | yes 10 min. | yes 10 min. | yes 10 min. | yes 5 min. |
| 13. Changes in Blood | causes leucocytosis | thromboses | yes | no influence |
| 14. Influence on lungs | causes inflammation | causes inflammation | yes, inflames | no influence |
| 15. Influence on kidney | strongly nephrotoxic | nephrotoxic | nephrotoxic | no influence |
| 16. Usage at home, hospitals, schools, and other institutions | impossible | impossible | with caution | can be used safely |

TABLE 7

| propeties | on concrete known | optimal option | asbestos cement known | optimal option | slate known | optimal option | steel -3 known | optimal option |
|---|---|---|---|---|---|---|---|---|
| water resistance water soluble $P_2O_5$, % | 0.01 | — | 0.05 | — | — | — | 0.05 | — |
| atmospheric stabilty month | 6 | 60 | 6 | 60 | 6 | 48 | 6 | 36 |
| solidity, (hardness) 3% in NaCl, month | 1 | 4 | 1 | 3 | 1 | 3 | 1 | 3 |
| solidity (hardness) on impact $kg/cm^2$ | 40 | 70 | 60 | 30 | 30 | 60 | 30 | 50 |
| solidity (hardness) on adhesion | | | | | | | 2 | 3.6 |

TABLE 8

Definition of solidification period

| contents of the composition massive % | | compression hardness | | | | | pH of pressed out water | | | |
|---|---|---|---|---|---|---|---|---|---|---|
| | | Delay hours | | | | | | | | |
| iron phosphate composition andesite - 70 | prototype | 1.2 | 1.5 | 2.2 | 2.5 | 2.5 | 4.5 | 5.2 | 5.9 | 6.5 | 6.5 |
| | optimal option | 2.5 | 2.5 | 3.0 | 3.0 | 3.0 | 5.0 | 5.5 | 6.5 | 6.5 | 6.5 |
| iron phosphate composition andesite - 70 kaoline - 10 | prototype | 1.8 | 2.5 | 3.5 | 4.0 | 4.0 | 4.0 | 5.5 | 6.5 | 7.0 | 7.0 |
| | optimal option | 4.0 | 4.0 | 5.5 | 5.5 | 5.5 | 5.0 | 5.5 | 6.5 | 6.5 | 6.5 |
| iron phosphate composition andesite - 80 | prototype | 0.2 | 0.3 | 0.5 | 0.5 | 0.5 | 3.0 | 3.0 | 3.0 | 3.5 | 3.5 |
| | optimal option | 3.5 | 4.0 | 4.5 | 4.5 | 4.5 | 5.5 | 5.5 | 6.0 | 6.5 | 6.5 |
| iron phosphate composition andesite - 80 (warmed up to 400°) | prototype | 4.0 | — | — | — | — | 7.0 | 7.0 | — | — | — |
| | optimal option | 5.0 | 5.0 | 5.0 | 5.0 | 5.0 | 7.0 | 7.0 | 7.0 | 7.0 | 7.0 |

LIST OF REFERENCES

1. Kopein V. A. "The material in regard to metalophosphate basis". Moscow, Publishing House "Chemistry", 1976, pp. 50–54.

2. Korbridge D. Phosphorus. Moscow, 1982, pp. 130–141.

3. USSR, Inventor's Certificate, N 968005, 1992.

4. USSR, Inventor's Certificate, N 1654281, 1991.

5. Deutsches Patentamt, Offenlegungsschrift N 2302216, 1974.

What is claimed is:

1. A phosphatic composition comprising a solution of the following ingredients, stated in parts by weight:

| | |
|---|---|
| orthophosphoric acid | about 100 |
| iron oxide | about 20–about 41 |
| metal powder | about 0.5–about 2.5 |
| water | about 30–about 70 | wherein the molar ratio of phosphate ion moiety in said orthophosphoric acid to iron ion moiety in said iron oxide in the composition is from 2 to 4.

2. A composition according to claim 1 wherein the metal powder is selected from the group consisting of aluminum, magnesium, zinc, calcium, cobalt, yttrium, nickel and scandium powders.

3. A composition according to claim 2 wherein the metal powder is aluminum powder.

4. A method of providing anti-microbial efficacy to materials and surfaces comprising applying a safe and effective amount of the composition of claim 1 to said materials and surfaces.

5. A method of providing a protective coating to a hard porous surface comprising the application of the composition of claim 1 in a coating on said surface.

* * * * *